Figure 1:
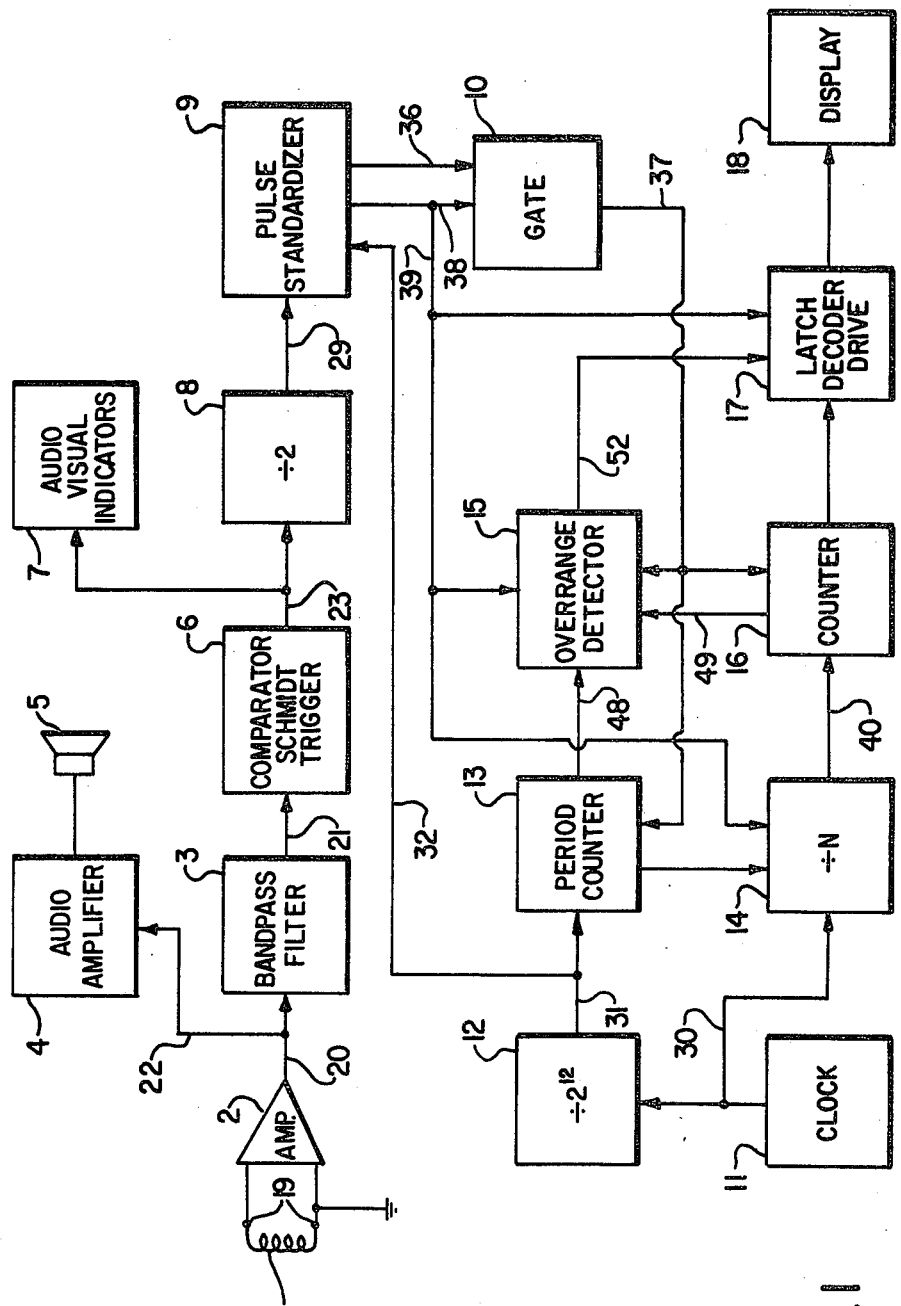

United States Patent [19]

Dyck et al.

[11] 4,436,096

[45] Mar. 13, 1984

[54] PORTABLE DIGITAL HEART RATE METER/STETHOSCOPE

[75] Inventors: Walter R. Dyck, Medicine Hat; Burns R. Hay, Calgary, both of Canada

[73] Assignee: Her Majesty the Queen in right of Canada, as represented by the Minister of National Defence, Ottawa, Canada

[21] Appl. No.: 231,442

[22] Filed: Feb. 4, 1981

[30] Foreign Application Priority Data

Apr. 24, 1980 [CA] Canada .................................. 350599

[51] Int. Cl.³ .............................................. A61B 5/02
[52] U.S. Cl. .................................................. 128/689
[58] Field of Search ................ 128/680, 681, 689–690, 128/715

[56] References Cited

U.S. PATENT DOCUMENTS

| | | | |
|---|---|---|---|
| 3,467,837 | 9/1969 | Vick | 128/680 X |
| 3,921,623 | 11/1975 | Okada et al. | 128/715 X |
| 3,978,848 | 9/1976 | Yen et al. | 128/681 |
| 4,058,118 | 11/1977 | Stupay et al. | 128/690 |
| 4,181,134 | 1/1980 | Mason et al. | 128/690 X |
| 4,220,160 | 9/1980 | Kimball et al. | 128/715 |
| 4,262,674 | 4/1981 | Uemura et al. | 128/689 X |

FOREIGN PATENT DOCUMENTS

741853  6/1980  U.S.S.R. ............................ 128/689

*Primary Examiner*—Kyle L. Howell
*Assistant Examiner*—Francis J. Jaworski
*Attorney, Agent, or Firm*—Cushman, Darby & Cushman

[57] ABSTRACT

Electrical signals corresponding to heart sounds detected by a pulse/sound transducer are filtered in a narrow bandpass filter whose pass band is centered on a characteristic heart sound frequency of 33 Hz. The filter improves signal-to-noise ratio and enables the transducer to be used over a patient's clothing. The unfiltered signal is amplified and fed to binaural leads to provide the function of an electronic stethoscope. In addition, the filtered signal is converted into pulses in response to which a count corresponding to the detected heart rate is established in a counter and displayed as a digital heart rate indication.

20 Claims, 3 Drawing Figures

PORTABLE DIGITAL HEART RATE METER/STETHOSCOPE

This invention relates to an electronic heart sound detector.

Medical personnel frequently require to know a patient's heart rate. A standard or an electronic stethoscope can be used to this end, but these do not provide heart rate readouts and instead the heart beats must be personally counted and a calculation performed to give the required result. This procedure is not only time consuming but also liable to error.

A rapid readout of a patient's heart rate is often desired. In addition, it is often desirable that the heart rate be detected, or heart sounds listened to, through the patient's clothing. This may be the case where speed is important or for the sake of convenience, or where the patient is trapped or is the subject of burns, or where the patient is in a harmful or toxic environment where protective clothing can not be removed. Standard stethoscopes require skin contact and therefore are unsuitable for use in such situations, whereas known electronic stethoscopes produce a high level of background noise, along with the desired signal, when used to detect heart sounds through clothing.

Devices are available which measure heart rate accurately from a patient's electrocardiogram, but these are bulky, heavy, and expensive and can not be used in many of the situations discussed above.

An object of this invention is to provide an improved heart sound detector which overcomes or substantially reduces at least some of the above disadvantages.

According to one aspect of this invention there is provided an electronic heart sound detector comprising a transducer for producing an unfiltered electrical signal in response to heart sounds; means for producing from the unfiltered electrical signal an indication of the heart sounds; means for producing from the filtered electrical signal, the detected heart rate as a digital display.

According to another aspect of this invention there is provided an electronic heart rate detector comprising a transducer for producing an electrical signal in response to heart sounds; a bandpass filter for filtering the electrical signal, the bandpass filter having a pass band including a characteristic heart sound frequency; means for producing pulses, corresponding to heart sounds, from the filtered electrical signal; counting means responsive to said pulses for producing a count corresponding to the heart rate of the heart sounds; and means for displaying said count as a detected heart rate.

In a preferred embodiment of the invention, the bandpass filter has a pass band centered on a frequency of substantially 33 Hz.

The invention is based on the recognition, which has been reported by Yoganathan et al. ("Use of the Fast Fourier Transform in the Frequency Analysis of the Second Heart Sound in Normal Man", Medical and Biological Engineering, July 1976, pages 455–460) and found by the present inventors, that heart sounds contain characteristic frequencies. The present inventors have established that the most common of these characteristic frequencies is approximately 33 Hz, and that by filtering detected heart sound signals at this frequency an enhanced signal-to-noise ratio is achieved, which enables more accurate detection of heart sounds and consequently more reliable heart rate determination, and facilitates the use of electronic stethoscope transducers to detect heart sounds through patient's clothing.

Whilst a frequency of 33 Hz has been determined and is utilized in the embodiment of the invention described herein, other characteristic heart sound frequencies may be determined by frequency analysis and could alternatively or additionally be utilized.

In a preferred embodiment of the heart rate detector the counting means comprises a first counter for counting clock pulses at a first frequency during periods between said pulses corresponding to heart sounds to establish a first count; means for frequency dividing clock pulses at a second frequency higher than the first frequency by the first count to produce resultant pulses; and means for counting said resultant pulses during said periods to produce said count, corresponding to the heart rate of the heart sounds, for display. The detector preferably includes means for generating said clock pulses at said second frequency, and means for frequency dividing said clock pulses at said second frequency to produce said clock pulses at said first frequency. Conveniently the second frequency is 1.118 MHz and the clock pulses are generated at this frequency by a crystal controlled oscillator and are frequency divided by a factor of $2^{12}$.

The means for producing pulses corresponding to heart sounds preferably comprises means, such as a comparator, Schmidt trigger, or monoflop, for producing a pulse in response to each of the first and second heart sounds in each heart cycle, and means for frequency dividing said pulses by a factor of 2 to produce a single pulse for each heart cycle.

In response to the pulses corresponding to heart sounds, a visual indication of detected heart sounds can be provided for example by a light-emitting diode, and/or an audible indication can be provided for example by a buzzer. Furthermore, the detector can include an audio amplifier responsive to the unfiltered electrical signal for providing an audio output signal for supply to an electro-acoustic transducer such as binaural leads, providing the function of an electronic stethoscope.

A buffer amplifier is conveniently coupled between the heart sound transducer and the bandpass filter.

The invention will be further understood from the following description by way of example of an embodiment thereof with reference to the accompanying drawings, in which:

FIG. 1 illustrates a block diagram of an electronic heart rate detector; and

Figure 2:
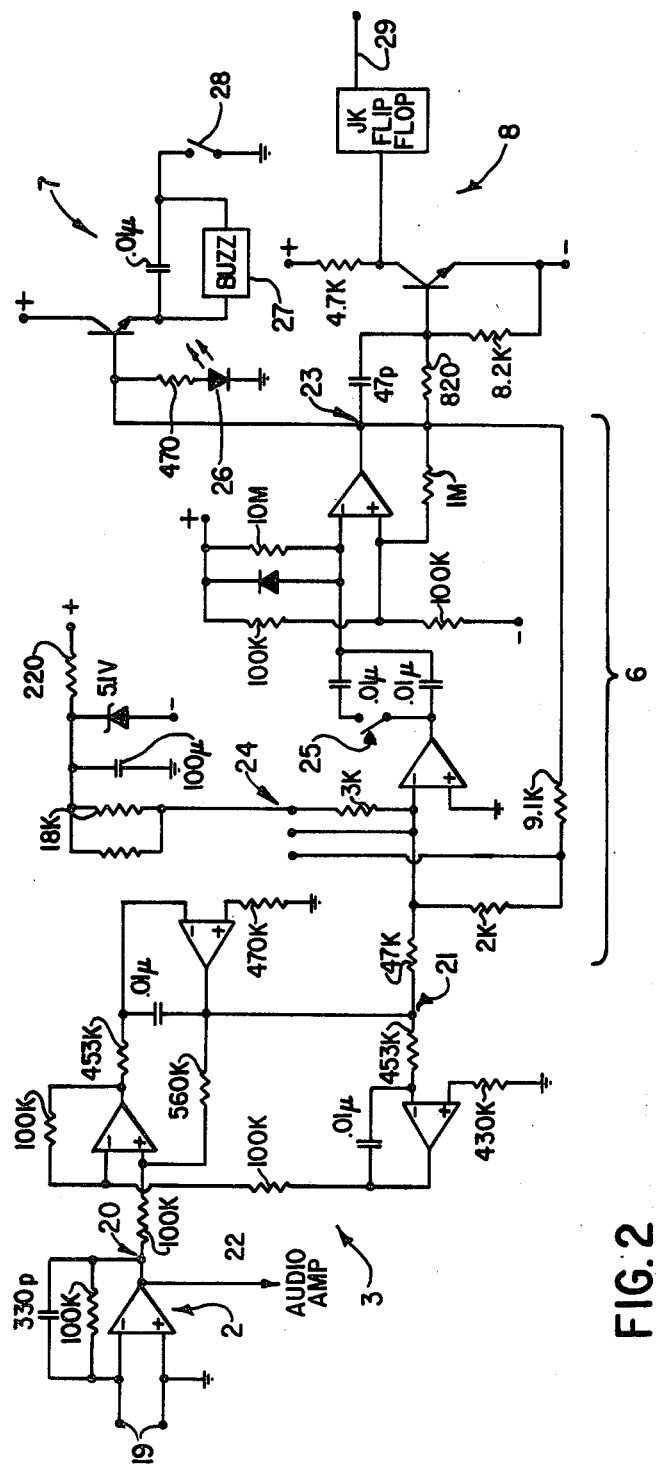
Figure 3:
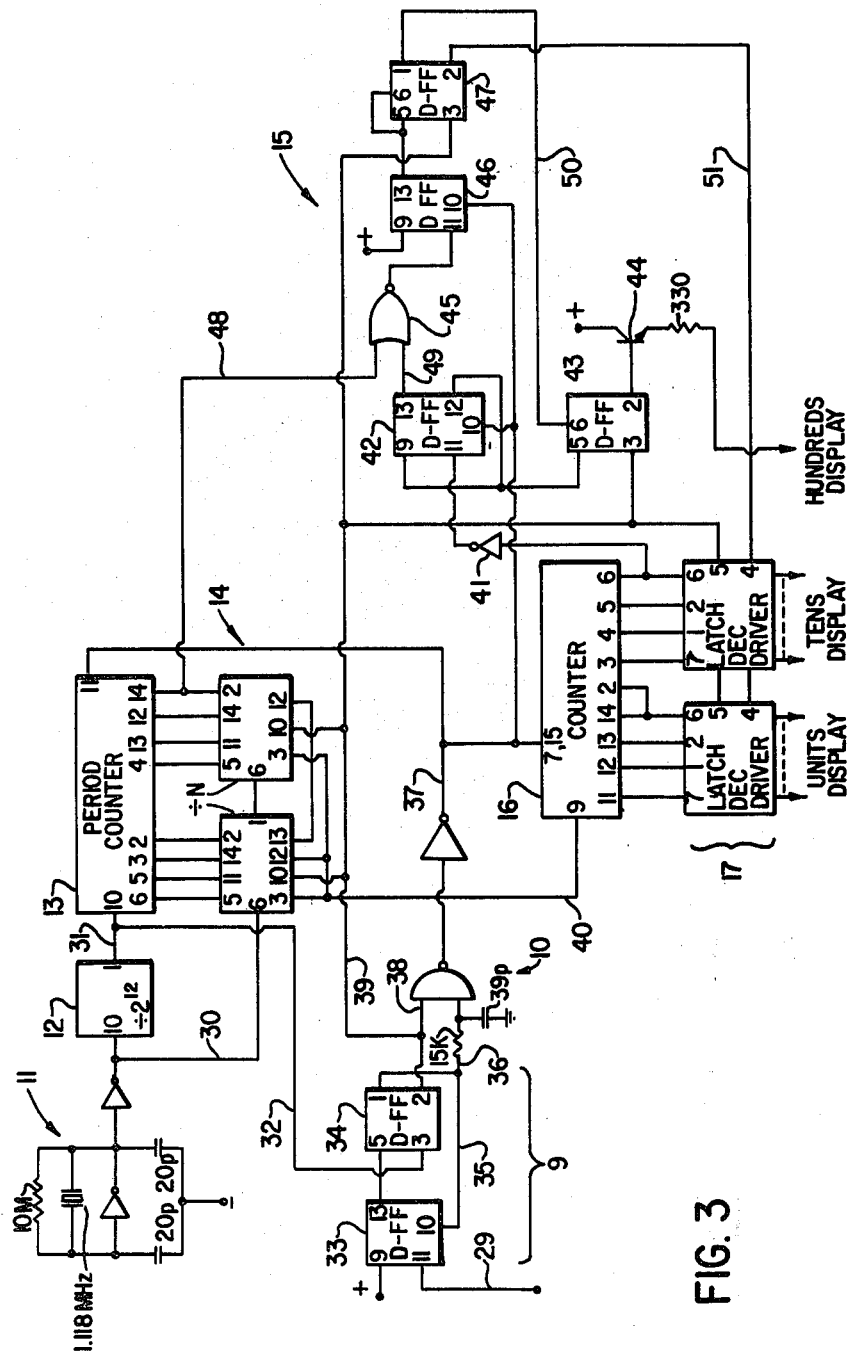

FIGS. 2 and 3 schematically illustrate in more detail parts of the detector of FIG. 1.

In the drawings, in which the same references are used in different figures to denote the same parts, FIG. 1 illustrates a preferred form of electronic heart rate detector, which comprises a known type of pulse/sound transducer 1, a buffer amplifier 2, a bandpass filter 3, an audio amplifier 4, an audio output 5, a comparator-Schmidt trigger circuit 6, audio and visual indicators 7, a ÷2 frequency divider 8, a pulse standardizer 9, a gate circuit 10, a clock pulse generator 11, a ÷$2^{12}$ frequency divider 12, a period counter 13, a ÷N frequency divider 14, an over-range detector 15, a counter 16, a latch/decoder/display driver stage 17, and a display 18.

FIG. 2 illustrates in more detail the buffer amplifier 2, bandpass filter 3, circuit 6, indicators 7, and frequency divider 8. FIG. 3 illustrates in more detail the components 9 to 17 of the detector. The differential amplifiers illustrated in FIG. 2 are all type LM124D, and the J-K flip-flop is type MC14027. As illustrated in FIG. 3 the gates and inverters are contained in a type MC14572 package, the frequency divider 12 and period counter 13 are type MC14040, the frequency divider 14 is constituted by two type MC14526 devices, the counter 16 is type MC14518, the stage 17 comprises two type MC14511 devices, and the D-type flip-flops are type MC14013. Pin designations of these device packages are indicated in FIG. 3. The detector can be arranged as a portable unit with integral power supplies (referred to as + and − in the drawings) of +3.75 volts and −2.5 volts with respect to ground.

Referring to FIGS. 1 and 2, the transducer 1, which is a conventional type of pulse/sound transducer as used in some types of electronic stethoscope, is connected to the input terminals 19 of the buffer amplifier 2. The output of this amplifier is conducted via a line 20 to the input of the bandpass filter 3, which is selected to have a narrow pass band centered at a characteristic heart sound frequency, in this case 33 Hz. The output of buffer amplifier 2 is also connected via a line 22 to the input of the audio amplifier 4 whose output is connected to the audio output 5, providing an audible signal corresponding to the detected heartbeat.

The bandpass filter illustrated in FIG. 2 is in the form of a high pass/low pass filter having an output at a point 21.

The point 21 is connected to the input of the comparator-Schmidt trigger circuit 6 whose output is referenced 23. The circuit 6 includes a switch 24 for setting the sensitivity of the circuit and a switch 25 for selection between fast and slow heartbeat rates. The output 23 is connected to the input of the indicator stage 7, which as illustrated in FIG. 2 comprises a light-emitting diode 26 for providing a visible indication of the detected heartbeat, and a buzzer 27 with a switch 28 for providing audible indications of the detected heartbeat, when required.

The output 23 of the circuit 6 is also connected to the input of the ÷2 frequency divider 8, which as shown in FIG. 2 comprises a transistor amplifier stage and a J-K flip-flop, the collector of the transistor being connected to the trigger input of the flip-flop and the Q output of the flip-flop being connected to an output line 29 of the frequency divider 8.

The operation of the parts of the detector as so far described is as follows:

In use, the transducer 1 is placed either directly on the chest of a patient, or on the patient's clothing, over the approximate vicinity of the heart, and the switches 24 and 25 are set appropriately. The transducer produces an electrical signal corresponding to the two heart sound bursts which occur in each heart cycle, and this signal is amplified by the buffer amplifier 2 and filtered by the bandpass filter 3. Because the bandpass filter 3 has a narrow pass band centered at a characteristic heart sound frequency, it passes the heart sound signals at this frequency. The signal produced at the point 21 at the output of the bandpass filter 3 has a much enhanced signal-to-noise ratio compared with that detected by the transducer and produced on the line 20, because a large part of the noise, which is picked up by the transducer 1 and which has a wide-band characteristic, is filtered out of the signal by the filter 3.

The unfiltered signal at point 20 is converted into an audible signal by the amplifier 4 and binaural output 5, providing the function of an electronic stethoscope.

The filtered signal at the point 21 is converted by the circuit 6 into a signal having two pulses per heart cycle, corresponding to the two detected heart sounds per heart cycle, at the output 23. These pulses activate the light-emitting diode 26 and buzzer 27 to provide visual and audio indications of the detected heart sounds, and are also divided in frequency by the ÷2 frequency divider 8 to produce on the line 29 a single pulse per heart cycle.

Referring now to FIGS. 1 and 3, the clock pulse generator 11 comprises a 1.118 MHz crystal and generates clock pulses at this frequency. These clock pulses are applied via a line 30 to a count input of the ÷N frequency divider 14, and also to an input of the ÷$2^{12}$ frequency divider 12 which consequently produces on an output line 31 clock pulses at a frequency of 273 Hz. The latter clock pulses are applied to a count input of the period counter 13 and via a line 32 to the clock input of a second one 34 of two D-type flip-flops 33 and 34 which constitute the pulse standardizer 9. The line 29 is connected to the clock input of the flip-flop 33, whose data input receives an enabling (+) voltage level and whose Q output is connected to the data input of the flip-flop 34. The $\overline{Q}$ output of the flip-flop 34 is connected to a resetting input of the flip-flop 33 via a line 35 and constitutes an output of the pulse standardizer 9 which is connected to an input 36 of the gate circuit 10 whose output is produced on a line 37. The line 37 is connected to resetting inputs of the period counter 13, the counter 16, and D-type flip-flops 42 and 46 referred to below. The Q output of the flip-flop 34 is connected to an input 38 of the gate circuit 10 and via a line 39 to enable inputs of the ÷N frequency divider 14, latch enable inputs of the latch/decoder/driver stage 17, and clock inputs of D-type flip-flops 43 and 47 referred to below.

Count outputs of the period counter 13 are connected to pre-setting inputs of the ÷N frequency divider 14, which produces pulses on an output line 40 which is connected to a clock input of the counter 16. Count outputs of the counter 16 are connected to inputs of the latch/decoder/driver stage 17 whose outputs are connected to the terminals of units and tens seven-segment indicators constituting part of the display 18. An output of the counter 16 is connected via an inverter 41 to the clock input of the D-type flip-flop 42 (which constitutes part of the counter 16 as illustrated in FIG. 1) whose $\overline{Q}$ output is connected to its data input and also to the data input of the D-type flip-flop 43. The flip-flop 43, and a transistor 44 to which its $\overline{Q}$ output is connected, constitute part of the latch/decoder/driver stage as illustrated in FIG. 1 and drive a 'hundreds' part of the display 18.

The overrange detector 15 consists of a NOR gate 45 and the D-type flip-flops 46 and 47. The gate 45 has its inputs connected via a line 48 to an overflow output of the period counter 13 and via a line 49 to the Q output of the flip-flop 42, and its output connected to the clock input of the flip-flop 46 whose data input is supplied with an enabling (+) voltage level. The Q output of the flip-flop 46 is connected to the data and setting inputs of the flip-flop 47, whose Q output is connected to a setting input of the flip-flop 43 via a line 50. The $\overline{Q}$ output of the flip-flop 47 is connected to a display blanking input of the units and tens parts of the latch/decoder/driver 17 via a line 51. The lines 50 and 51 in FIG. 3 are represented by the single line 52 in FIG. 1.

The operation of this part of the detector is as follows:

For each pulse which occurs on the line 29, and hence for each detected heart cycle, the pulse standardizer 9 produces on the line 39 a pulse of precise duration, corresponding to the period of the clock pulses on the line 32. This duration is 1/273 Hz, or 3.66 ms. For each such pulse the gate circuit 10 produces on the line 37 a narrow resetting pulse which resets the period counter 13, the counter 16 and flip-flop 42, and the flip-flop 46 in the overrange detector 15. Between successive resetting pulses, the period counter 13 counts pulses of the 273 Hz clock on the line 31. Each 3.66 ms duration pulse produced on the line 39 enables the ÷N frequency divider 14 to divide the 1.118 MHz clock pulses on the line 30 by the count reached by the period counter 13 and to produce pulses corresponding to the quotient on the line 40. These pulses are counted by the counter 16 and the count is displayed on the display 18. If the detected heart rate is outside of a predetermined range (16 to 199 beats per minute) the overrange detector 15 is triggered, via the line 48 if the rate is too low and via the line 49 if the rate is too high, to blank the display via the line 51.

The following examples further illustrate this operation:

(a) If the detected heart rate is 60 beats per minute, 1 pulse per second occurs on the line 29. The period counter 13 is arranged to count up at one quarter of the 273 Hz clock pulse rate, i.e. at 273/4=68 pulses per second, so that between successive resetting pulses on the line 37 it counts to 68. During the 3.66 ms pulse on the line 39, 1118000×0.00366=4091 pulses occur on the line 30, and these pulses are divided by 68 in the ÷N frequency divider 14 to produce 4091/68=60 pulses on the line 40. These pulses are counted by the counter 16, stored in the stage 17 and the heart rate of 60 beats per minute is displayed on the display 18.

(b) If the heart rate is 30 beats per minute, the period counter counts to 136 between successive resetting pulses, the ÷N divider 14 produces 4091/136=30 pulses on the line 40, and these are counted by the counter 16 and 30 is displayed on the display 18.

(c) If the heart rate is 120 beats per minute, the period counter counts to 34 between successive resetting pulses, the divider 14 produces 4091/34=120 pulses on the line 40 during the 3.66 ms enabling pulse duration, and the resultant count of 120 is displayed on the display 18.

(d) If the heart rate is 15 beats per minute, the period counter 13 would count to 272 between successive resetting pulses. This is outside of the preset enable range of the divider 14. The period counter 13 in this case produces a change of state on the line 48 which triggers the overrange detector 15 to blank the display 18.

(e) If the heart rate is 240 beats per minute, the period counter counts to 17 and the divider 14 produces 4091/17=240 pulses on the line 40. This is over the range (199) of the display 18, and in this case the flip-flop 42 produces a change of state on the line 99 which triggers the overrange detector 15 to blank the display 18.

Numerous variations, modifications, and adaptations may be made to the above described embodiment of the invention without departing from the scope of the invention as defined in the claims. For example, different forms of and arrangements of analog and digital circuitry may be used. In particular, the bandpass filter may be of a different form, for example it may be constituted by a bi-quad filter, and a comparator feedback network could be used for detecting the heart sound signals. In addition, with appropriate modification of the counting circuitry the ÷2 frequency divider 8 could be dispensed with. Furthermore, different clock pulse frequencies from those described may be used.

In addition, the bandpass filter center frequency need not necessarily be limited to the 33 Hz characteristic heart sound frequency discussed above, but may be selected to be any other characteristic heart sound frequency which can be determined by frequency analysis of heart sounds.

The embodiments of the invention in which an exclusive property or privilege is claimed are defined as follows:

1. An electronic heart rate detector comprising:
a transducer for providing an electrical signal in response to sounds, including heart sounds;
filter means for filtering said electrical signal, said filter means having a passband including frequencies characteristic of heart sounds and producing a filtered electrical signal;
means for detecting amplitude levels of said filtered electrical signal exceeding a predetermined threshold level and providing an output pulse of fixed duration in response to each amplitude level exceeding said threshold level, the output of said detecting means being connected to the input thereof, said detecting means including a comparator having an input connected to the output of said filter means for producing a first output pulse in response to each filtered electrical signal amplitude level exceeding said threshold level, the duration of said first output pulse corresponding to the duration of that portion of said amplitude level exceeding said threshold level; means for selectively modifying the duration of said output pulse; means responsive to the output of said pulse modifying means for producing a second output pulse of predetermined duration, the output of said second output pulse producing means being connected to the input of said comparator; and
means responsive to the output of said second output pulse producing means for producing a signal representative of a heart rate; and
means for displaying said signal as a detected heart rate.

2. A detector as claimed in claim 1 wherein the counting means comprises a first counter for counting clock pulses at a first frequency during periods between said pulses corresponding to heart sounds to establish a first count; means for frequency dividing clock pulses at a second frequency higher than the first frequency by the first count to produce resultant pulses; and means for counting said resultant pulses during said periods to produce said count, corresponding to the heart rate of the heart sounds, for display.

3. A detector as claimed in claim 2 and including means for generating said clock pulses at said second frequency, and means for frequency dividing said clock pulses at said second frequency to produce said clock pulses at said first frequency.

4. A detector as claimed in claim 1 wherein the means for producing pulses corresponding to heart sounds comprises means for producing a pulse in response to each of the first and second heart sounds in each heart cycle, and means for frequency dividing said pulses by a factor of 2 to produce a single pulse for each heart cycle.

5. A detector as claimed in claim 1 and including means for providing a visual indication of detected heart sounds responsive to said pulses corresponding to heart sounds.

6. A detector as claimed in claim 1 and including means for providing an audible indication of detected heart sounds responsive to said pulses corresponding to heart sounds.

7. A detector as claimed in claim 1 and including an audio amplifier responsive to the unfiltered electrical signal for providing an audio output signal for supply to an electro-acoustic transducer.

8. A detector as claimed in claim 1 and including a buffer amplifier coupled between said transducer and said bandpass filter.

9. A detector as claimed in claim 1 or 2 wherein the bandpass filter has a pass band centred on a frequency of substantially 33 Hz.

10. A detector as claimed in claim 3, 4, or 5 wherein the bandpass filter has a pass band centred on a frequency of substantially 33 Hz.

11. A detector as claimed in claim 6, 7, or 8 wherein the bandpass filter has a pass band centred on a frequency of substantially 33 Hz.

12. A detector as defined in claim 1, said detector means including:
a comparator having an input connected to the output of said filter for producing a first output pulse in response to each filtered electrical signal amplitude level exceeding said threshold level, the duration of said first output pulse corresponding to the duration of that portion of said amplitude level exceeding said threshold level;
means for selectively modifying the duration of said output pulses;
means responsive to the output of said pulse modifying means for producing a second output pulse of predetermined duration, the output of said second output pulse producing means being connected to the input of said comparator; and
said heart rate signal producing means being responsive to the output of said second output pulse producing means.

13. A detector as defined in claim 1, said detecting means including means for adjusting said threshold level.

14. A detector as defined in claim 1, said threshold level being set for detecting amplitude levels representing the first and second heart sounds of each heart cycle.

15. A detector as defined in claim 1, further including an audio amplifier connected to the output of said transducer and providing an audio output of said electrical signal for supply to an electro-acoustic transducer.

16. A detector as defined in claim 1, further including means connected to the output of said detecting means for providing visual and audible indications of detected heart sounds.

17. An electronic heart rate detector, comprising:
a transducer for converting sounds, including heart sounds, to an electrical signal;
an audio amplifier connected to the output of said transducer and providing an audio output of said electrical signal for supply to an electro-acoustic transducer;
a bandpass filter for filtering said electrical signal and producing a filtered electrical signal, said filter having a passband centered on a frequency of about 33 Hz;
means for detecting the first and the second heart sounds of a heart cycle and providing an indication of said heart sounds, said means including a comparator having an input connected to the output of said filter for producing a first output pulse corresponding to each filtered electrical signal amplitude level exceeding a predetermined threshold level, the duration of said first output pulse corresponding to the duration that said amplitude level exceeds said threshold level, means for selectively adjusting said threshold level to detect said first and said second heart sounds of a heart cycle, means for selectively modifying the duration of said first output pulses, means responsive to the output of said pulse modifying means for producing a second output pulse of predetermined duration, the output of said second output pulse producing means being connected to the input of said comparator;
means responsive to said second output pulses for producing a visual and audible indication of heart sounds;
means responsive to said second output pulses for producing a signal representative of the heart rate of detected heart sounds; and
means responsive to said representative signal for providing a visual digital display of said heart rate.

18. A detector as claimed in claim 17 wherein said representative signal producing means including means having a first counter for counting clock pulses at a first frequency during periods between said second pulses corresponding to heart sounds to establish a first count; means for frequency dividing clock pulses at a second frequency higher than the first frequency by the first count to produce resultant pulses; and means for counting said resultant pulses during said periods to produce said count, corresponding to the heart rate of the heart sounds, for display.

19. A detector as claimed in claim 18 and including means for generating said clock pulses at said second frequency, and means for frequency dividing said clock pulses at said second frequency to produce said clock pulses at said first frequency.

20. A detector as claimed in claim 17 further including means for frequency dividing said second pulses by a factor of 2 to produce a signal pulse for each heart cycle.

* * * * *